(12) United States Patent
Vidyasagar et al.

(10) Patent No.: US 11,529,325 B2
(45) Date of Patent: *Dec. 20, 2022

(54) MATERIALS AND METHODS FOR IMPROVING LUNG FUNCTION AND FOR PREVENTION AND/OR TREATMENT OF RADIATION-INDUCED LUNG COMPLICATIONS

(71) Applicant: UNIVERSITY OF FLORIDA RESEARCH FOUNDATION, INCORPORATED, Gainesville, FL (US)

(72) Inventors: Sadasivan Vidyasagar, Gainesville, FL (US); Paul Okunieff, Gainesville, FL (US)

(73) Assignee: UNIVERSITY OF FLORIDA RESEARCH FOUNDATION, INCORPORATED, Gainsville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/987,469

(22) Filed: Aug. 7, 2020

(65) Prior Publication Data

US 2021/0038551 A1 Feb. 11, 2021

Related U.S. Application Data

(63) Continuation of application No. 16/508,854, filed on Jul. 11, 2019, now Pat. No. 10,758,507, which is a continuation of application No. 14/773,960, filed as application No. PCT/US2014/023363 on Mar. 11, 2014, now Pat. No. 10,350,185.

(60) Provisional application No. 61/775,754, filed on Mar. 11, 2013.

(51) Int. Cl.
| | |
|---|---|
| A61K 31/198 | (2006.01) |
| A61K 31/405 | (2006.01) |
| A61K 33/14 | (2006.01) |
| A61K 9/00 | (2006.01) |

(52) U.S. Cl.
CPC .......... *A61K 31/198* (2013.01); *A61K 9/0053* (2013.01); *A61K 31/405* (2013.01); *A61K 33/14* (2013.01)

(58) Field of Classification Search
CPC ................ A61K 31/198; A61K 31/405; A61K 9/0053; A61K 33/14
USPC ....................................................... 514/564
See application file for complete search history.

(56) References Cited

U.S. PATENT DOCUMENTS

2012/0077748 A1* 3/2012 Vidyasagar ............... A61P 1/12
514/23

OTHER PUBLICATIONS

Laiakis et al. in Advances in Space Research 39, 1019-1025 (2007) (Year: 2007).*
Seville et al., (PowderTechnology, 2007, 178, 40-50) (Year: 2007).*

* cited by examiner

*Primary Examiner* — Yevgeny Valenrod
(74) *Attorney, Agent, or Firm* — Greenberg Traurig LLP

(57) ABSTRACT

The subject invention provides therapeutic compositions and uses thereof for improving pulmonary function. In one embodiment, the therapeutic composition comprises one or more free amino acids selected from lysine, glycine, threonine, valine, tyrosine, aspartic acid, isoleucine, tryptophan, asparagine, and serine; and electrolytes. In one embodiment, the subject invention can be used to prevent or treat long-term lung complications induced by radiation.

15 Claims, 4 Drawing Sheets

MATERIALS AND METHODS FOR IMPROVING LUNG FUNCTION AND FOR PREVENTION AND/OR TREATMENT OF RADIATION-INDUCED LUNG COMPLICATIONS

CROSS-REFERENCE TO A RELATED APPLICATION

This application is a Continuation Application of U.S. application Ser. No. 16/508,854, filed Jul. 11, 2019, which is a Continuation Application of U.S. application Ser. No. 14/773,960, now U.S. Pat. No. 10,350,185, filed Sep. 9, 2015, which is a U.S. National Stage Application of International Application No. PCT/US2014/023363, filed Mar. 11, 2014, which claims the benefit of U.S. provisional application Ser. No. 61/775,754, filed Mar. 11, 2013, all of which are incorporated herein by reference in their entirety.

BACKGROUND OF INVENTION

Radiation therapy, a common treatment for malignancies, can cause severe damage to the lung—a highly radiosensitive organ. Radiation can cause a broad spectrum of pneumopathies, including acute-phase alveolitis/pneumonitis, late-stage chronic pulmonary fibrosis, and various respiratory dysfunctions such as dyspnea and pulmonary edema.

During the acute phase of radiation-induced lung injury, inflammation is the predominant histological and physiologic feature. The initial injury to lung tissues results in infiltration of inflammatory cells, such as macrophages and neutrophils; focal accumulation of mononuclear cells; increased levels of inflammatory cytokines such as transforming growth factor-$\beta$ (TGF-$\beta$), interleukin-1$\alpha$ (IL-1$\alpha$), and tumor necrosis factor (TNF$\alpha$); and a decline in pulmonary function.

Radiation also induces late-stage pulmonary fibrosis—an insidious fibroproliferative condition characterized by a gradual, irreversible replacement of normal parenchyma cells with fibrous, connective, matrix macromolecules (e.g., collagens, fibronectins and proteoglycans) on and within the lungs, usually at sites of injury or infection. The excessive formation of fibrous tissue, resulting from the activation and proliferation of fibroblast cells, destructs normal lung structure and function. For instance, the accumulation of fibrous tissue thickens alveolar walls, obliterates air space, and causes epithelial injury or even alveolar collapse.

Patients suffering from pneumopathies (such as pneumonitis and pulmonary fibrosis) experience a varying degree of exertional dyspnea, and in late stages, orthopnea, cyanosis, and respiratory failure. Currently, there is no cure for radiation-induced pulmonary fibrosis. Median survival of radiation-induced pulmonary fibrosis is about 2-3 years.

Radiation-induced pneumopathy not only causes devastating effects on the quality of patient life, but sometimes can be even more life-threatening than the primary tumor or cancer. Consequently, the risk of radiation-induced pneumopathy, such as pulmonary fibrosis, has become a major dose-limiting factor and sometimes even prevents the use of radiation therapy.

There is a need for therapeutic formulations for prevention and treatment of radiation-induced lung injury and complications. As will be clear from the disclosures that follow, these and other benefits are provided by the subject invention.

BRIEF SUMMARY

The subject invention provides materials and methods for improving pulmonary function. In one embodiment, the subject invention is useful for the prevention and/or treatment of radiation-induced lung injury and lung complications, including radiation-induced alveolitis, pneumonitis, and pulmonary fibrosis.

In one embodiment, a composition of the subject invention is formulated for oral administration. In another embodiment, the composition is formulated for pulmonary administration.

In a preferred embodiment, the subject invention provides a method for improving pulmonary function, and/or for the prevention and/or treatment of radiation-induced lung injury and lung complications, wherein the method comprises administering, to a patient or subject in need of such treatment, an effective amount of a composition comprising, consisting essentially of, or consisting of L-lysine, L-glycine, L-threonine, L-valine, L-tyrosine, L-aspartic acid, L-isoleucine, and L-serine; one or more electrolytes selected from $Na^+$, $Ca^{2+}$, $Mg^{2+}$, $HCO_3^-$, and $Cl^-$; and optionally, therapeutically acceptable carriers, buffering agents, and flavoring agents.

In one embodiment, the total osmolarity of the therapeutic composition is from about 165 mOsm to 300 mOsm, or any value therebetween. In one embodiment, the composition has a pH from about 2.0 to 8.6, or any value therebetween.

In one embodiment, the subject invention can be used to prevent and/or treat lung complications induced by radiation. In one specific embodiment, the subject invention can be used to prevent and/or treat lung complications induced by ionizing radiation. In certain embodiments, the subject invention can be used to prevent and/or treat radiation-induced lung complications including, but not limited to, alveolitis, pneumonitis, and pulmonary fibrosis.

In certain embodiments, the present invention can be used to treat lung diseases including bronchial asthma, pneumonia, bronchiectasis, interstitial lung diseases, acute and/or chronic pneumonitis, chronic obstructive pulmonary disease (COPD), asthma, silicosis, and lung injury.

DETAILED DISCLOSURE

Figure 1A:
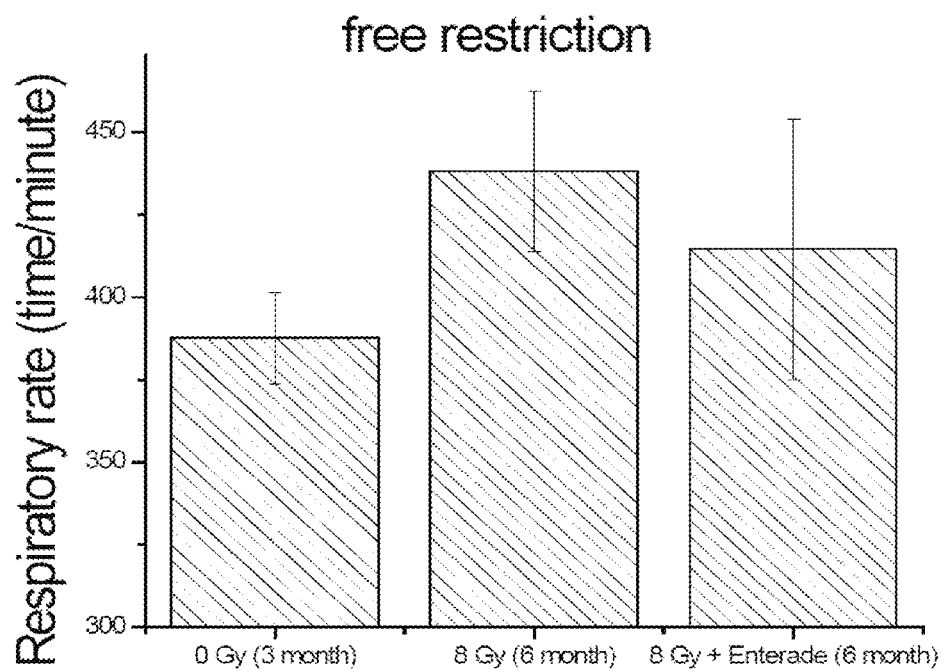
FIG. 1A-H shows the results of pulmonary function tests. Briefly, mice received radiation at a dose of 8 Gy. Twenty-four hours after irradiation, mice are treated with a therapeutic composition of the subject invention for a period of 14 days. Six months after irradiation, mice treated in accordance with the subject invention have improved function, when compared to control. The data show that the therapeutic composition improves pulmonary function and can be used to treat long-term lung complications induced by radiation.

The subject invention provides therapeutic compositions and methods for improving pulmonary function. In one embodiment, the subject invention is useful for the prevention and/or treatment of radiation-induced lung injury and lung complications, including radiation-induced alveolitis, pneumonitis, and pulmonary fibrosis.

In one embodiment, the composition is formulated for oral administration. In another embodiment, the composition is formulated for pulmonary administration.

In a preferred embodiment, the subject invention provides a method for improving pulmonary function, and/or for the prevention and/or treatment of radiation-induced lung injury and lung complications, wherein the method comprises administering, to a patient or subject in need of such treatment, an effective amount of a composition comprising, consisting essentially of, or consisting of L-lysine, L-glycine, L-threonine, L-valine, L-tyrosine, L-aspartic acid, L-isoleucine, and L-serine; one or more electrolytes selected from Na$^+$, Ca$^{2+}$, Mg$^{2+}$, HCO$_3^-$, and Cl$^-$; and optionally, therapeutically acceptable carriers, buffering agents, and flavoring agents.

The composition can be administered to a patient or subject immediately before, during, and/or after injury to the lungs, and can be administered once or multiple times each day.

Advantageously, in one embodiment, the compositions of the subject invention can be used to prevent or treat radiation-induced long-term lung complications. In one embodiment, mice that received radiation at a dose of 8 Gy are treated with the composition of the subject invention starting from 24 hours after irradiation, for a period of 14 days. Six months after irradiation, pulmonary function test, electrophysiology, radiological and histopathological examinations are performed. Mice treated with a composition of the subject invention exhibit improved pulmonary function, electrophysiology, radiological, and histopathological features, when compared to control.

Therapeutic Compositions for Improving Pulmonary Function

In one embodiment, the subject invention provides a therapeutic composition for improving pulmonary function, wherein the composition comprises, consists essentially of, or consists of one or more free amino acids selected from lysine, glycine, threonine, valine, tyrosine, aspartic acid, isoleucine, tryptophan, asparagine, and serine; and optionally, therapeutically acceptable carriers, electrolytes, buffering agents, and flavoring agents.

In one embodiment, the subject invention provides a therapeutic composition for improving pulmonary function, wherein the composition comprises, consists essentially of, or consists of lysine, glycine, threonine, valine, tyrosine, aspartic acid, isoleucine, tryptophan, and serine; and optionally, therapeutically acceptable carriers, electrolytes, buffering agents, and flavoring agents.

In another embodiment, the subject invention provides a therapeutic composition for improving pulmonary function, wherein the composition comprises, consists essentially of, or consists of lysine, glycine, threonine, valine, tyrosine, aspartic acid, isoleucine, and serine; and optionally, therapeutically acceptable carriers, electrolytes, buffering agents, and flavoring agents.

In one embodiment, the subject invention provides a therapeutic composition for improving pulmonary function, wherein the composition comprises, consists essentially of, or consists of one or more free amino acids selected from L-lysine, L-glycine, L-threonine, L-valine, L-tyrosine, L-aspartic acid, L-isoleucine, L-tryptophan, L-asparagine, and L-serine; and optionally, therapeutically acceptable carriers, electrolytes, vitamins, buffering agents, and flavoring agents.

In one embodiment, the subject invention provides a therapeutic composition for improving pulmonary function, wherein the composition comprises, consists essentially of, or consists of L-lysine, L-glycine, L-threonine, L-valine, L-tyrosine, L-aspartic acid, L-isoleucine, L-tryptophan, and L-serine; and optionally, therapeutically acceptable carriers, electrolytes, buffering agents, and flavoring agents.

In another embodiment, the subject invention provides a therapeutic composition for improving pulmonary function, wherein the composition comprises, consists essentially of, or consists of L-lysine, L-glycine, L-threonine, L-valine, L-tyrosine, L-aspartic acid, L-isoleucine, and L-serine; and optionally, therapeutically acceptable carriers, electrolytes, buffering agents, and flavoring agents.

In one embodiment, the free amino acids contained in the therapeutic composition can be present in neural or salt forms.

In one embodiment, the therapeutic composition further comprises one or more electrolytes selected from Na$^+$, Ca$^{2+}$, Mg$^{2+}$, HCO$_3^-$, CO$_3^{2-}$, and Cl$^-$.

In one embodiment, the total osmolarity of the composition is from about 165 mOsm to 300 mOsm, or any value therebetween including, but not limited to, 230 mOsm to 280 mOsm, 250 mOsm to 260 mOsm, and 200-220 mOsm. In another embodiment, the composition has a total osmolarity that is any value lower than 165 mOsm.

In certain embodiments, each free amino acid can be present at a concentration from 4 mM to 40 mM, or any value therebetween, wherein the total osmolarity of the composition is from about 230 mOsm to 280 mOsm. Alternatively, if the amino acid concentration is calculated based on mg/l, each free amino acid can be present at a concentration from 100 mg/l to 8000 mg/L, or any value therebetween, wherein the total osmolarity of the composition is from about 240 mOsm to 280 mOsm.

In certain specific embodiments, the therapeutic composition comprises one or more free amino acids present at their respective concentrations as follows: lysine at a concentration of about 730 to 6575 mg/l, or any value therebetween; aspartic acid at a concentration of about 532 to 4792 mg/l, or any value therebetween; glycine at a concentration of about 300 to 2703 mg/l, or any value therebetween; isoleucine at a concentration of about 525 to 4722 mg/l, or any value therebetween; threonine at a concentration of about 476 to 4288 mg/l, or any value therebetween; tyrosine at a concentration of about 725 to 6523 mg/l, or any value therebetween; valine at a concentration of about 469 to 4217 mg/l, or any value therebetween; tryptophan at a concentration of about 817 to 7352 mg/l, or any value therebetween; asparagine at a concentration of about 528 to 4756 mg/l, or any value therebetween; and/or serine at a concentration of about 420 to 3784 mg/l, or any value therebetween; wherein the total osmolarity of the composition is from about 165 mOsm to 300 mOsm, or any value therebetween.

In certain specific embodiments, the therapeutic composition comprises one or more free amino acids present at their respective concentrations as follows: lysine at a concentration of about 730 to 6575 mg/l, or any value therebetween; aspartic acid at a concentration of about 532 to 4792 mg/l, or any value therebetween; glycine at a concentration of about 300 to 2703 mg/l, or any value therebetween; isoleucine at a concentration of about 525 to 4722 mg/l, or any value therebetween; threonine at a concentration of about 100 to 4288 mg/l, or any value therebetween; tyrosine at a concentration of about 725 to 6523 mg/l, or any value therebetween; valine at a concentration of about 469 to 4217 mg/l, or any value therebetween; and/or serine at a concentration of about 420 to 3784 mg/l, or any value therebetween; wherein the total osmolarity of the composition is from about 165 mOsm to 300 mOsm, or any value therebetween.

In one embodiment, the subject invention provides a formulation comprising the following constituents: lysine (11-21 mOsm), aspartic acid (3-13 mOsm), glycine (19-29 mOsm), isoleucine (19-29 mOsm), threonine (19-29 mOsm), tyrosine (0.5-5 mOsm), valine (19-29 mOsm), tryptophan (5-20 mOsm), asparagine (3-13 mOsm), and/or serine (3-8 mOsm), or a subset of these ingredients.

In one embodiment, the composition has a pH from about 2.0 to 8.6, or any value therebetween. In certain embodiments, the composition has a pH from about 2.0 to 5.0, or any value therebetween, including, such as 2.0 to 4.2 and 2.0 to 3.6. In certain embodiments, the composition has a pH from about 7.3 to 7.5, or any value therebetween including, such as about 7.4. In certain embodiments, the composition has a pH from about 4.0 to 8.5, or any value therebetween including, such as 5.0 to 8.2, 6.0 to 8.0, 7.1 to 7.9, and about 7.4.

In a specific embodiment, the composition of the subject invention does not comprise glucose, glutamine, methionine, and/or lactose.

In one specific embodiment, the composition comprises lysine, glycine, threonine, valine, and tyrosine in a form of free amino acids. In a further specific embodiment, the composition comprises lysine, glycine, threonine, valine, tyrosine, aspartic acid, isoleucine, tryptophan, asparagine, and serine in a form of free amino acids.

In a further embodiment, the composition comprises one or more dipeptides that are made of the same or different amino acids selected from lysine, glycine, threonine, valine, tyrosine, aspartic acid, isoleucine, tryptophan, asparagine, or serine.

In one embodiment, the composition does not contain glutamine and/or methionine; and any di-, oligo-, or polypeptides or proteins that can be hydrolyzed into glutamine and/or methionine.

In an alternative embodiment, the composition may comprise free amino acid glutamine, and, optionally, one or more glutamine-containing dipeptides, wherein the total concentration of the free amino acid glutamine and the glutamine-containing dipeptide(s) is less than 300 mg/l, or any concentrations lower than 300 mg/l, such as 100 mg/l, 50 mg/l, 10 mg/l, 5 mg/l, 1 mg/l, 0.5 mg/l, or 0.01 mg/l.

In another alternative embodiment, the therapeutic composition may comprise free amino acid methionine, and, optionally, one or more methionine-containing dipeptides, wherein the total concentration of the free amino acid methionine and the methionine-containing dipeptide(s) is less than 300 mg/l, or any concentrations lower than 300 mg/l, such as 100 mg/l, 50 mg/l, 10 mg/l, 5 mg/l, 1 mg/l, 0.5 mg/l, or 0.01 mg/l.

In one embodiment, the therapeutic composition does not contain any saccharides, including any mono-, di-, oligo-, polysaccharides, and carbohydrates. In one specific embodiment, the therapeutic composition does not contain glucose, and/or any di-, oligo, polysaccharides, and carbohydrates that can be hydrolyzed into glucose. In a specific embodiment, the composition does not contain lactose. In another specific embodiment, the therapeutic composition does not contain fructose and/or galactose, and/or any di-, oligo-, polysaccharides, and carbohydrates that can be hydrolyzed into fructose and/or galactose.

In an alternative embodiment, the therapeutic composition may comprise monosaccharide glucose, and, optionally, one or more glucose-containing disaccharides other than lactose, wherein the total concentration of the monosaccharide glucose and the glucose-containing disaccharide(s) is less than 3 g/l, or any concentrations lower than 3 g/l, such as 1 g/l, 500 mg/l, 300 mg/l, 100 mg/l, 50 mg/l, 10 mg/l, 5 mg/l, 1 mg/l, 0.5 mg/l, or 0.01 mg/l.

In certain embodiments, the therapeutic composition comprises one or more electrolytes selected from, for example, $Na^+$; $K^+$; $HCO_3^-$; $CO_3^{2-}$; $Ca^{2+}$; $Mg^{2+}$; $Fe^2$; $Cl^-$; phosphate ions, such as $H_2PO_4^-$, $HPO_4^{2-}$, and $PO_4^{3-}$; zinc; iodine; copper; iron; selenium; chromium; and molybdenum. In an alternative embodiment, the composition does not contain $HCO_3^-$ or $CO_3^{2-}$. In another alternative embodiment, the composition comprises $HCO_3^-$ and $CO_3^{2-}$ at a total concentration of less than 5 mg/l, or concentrations lower than 5 mg/l.

In a further embodiment, the therapeutic composition comprises one or more vitamins including, but not limited to, vitamin A, vitamin C, vitamin D (e.g., vitamin $D_1$, $D_2$, $D_3$, $D_4$, and/or $D_5$), vitamin E, vitamin $B_1$ (thiamine), vitamin $B_2$ (e.g., riboflavin), vitamin $B_3$ (e.g., niacin or niacinamide), vitamin $B_5$ (pantothenic acid), vitamin $B_6$ (pyridoxine), vitamin $B_7$ (biotin), vitamin $B_9$ (e.g., folate or folic acid), vitamin $B_{12}$ (cobalamin), and vitamin K (e.g., vitamin $K_1$, $K_2$, $K_3$, $K_4$, and $K_5$), and choline.

In certain embodiments, the composition does not contain one or more of the ingredients selected from oligo-, polysaccharides, and carbohydrates; oligo-, or polypeptides or proteins; lipids; small-, medium-, and/or long-chain fatty acids; and/or food containing one or more above-mentioned nutrients.

In one embodiment, phosphate ions, such as $H_2PO_4^-$, $HPO_4^{2-}$, and $PO_4^{3-}$, are used to buffer the composition of the subject invention. In one embodiment, the therapeutic composition uses $HCO_3^-$ or $CO_3^{2-}$ as a buffer. In another embodiment, the therapeutic composition does not use $HCO_3^-$ or $CO_3^{2-}$ as buffer.

The term "consisting essentially of," as used herein, limits the scope of the ingredients and steps to the specified materials or steps and those that do not materially affect the basic and novel characteristic(s) of the present invention, i.e., compositions and methods for improving pulmonary function. For instance, by using "consisting essentially of," the therapeutic composition does not contain any unspecified ingredients including, but not limited to, free amino acids, di-, oligo-, or polypeptides or proteins; and mono-, di-, oligo-, polysaccharides, and carbohydrates that have a direct beneficial or adverse therapeutic effect on pulmonary function. Also, by using the term "consisting essentially of," the composition may comprise substances that do not have therapeutic effects on pulmonary function; such ingredients include carriers, excipients, adjuvants, flavoring agents, etc that do not affect pulmonary function.

The term "oligopeptide," as used herein, refers to a peptide consisting of three to twenty amino acids. The term "oligosaccharides," as used herein, refers to a saccharide consisting of three to twenty monosaccharides.

Improvement of Pulmonary Function

In one embodiment, the subject invention provides a method for improving pulmonary function, wherein the method comprises administering, to a subject in need of such treatment, a therapeutic composition of the invention.

In one embodiment, the composition is formulated for oral administration. In another embodiment, the composition is formulated for pulmonary administration.

In one specific embodiment, the subject invention provides a method for improving pulmonary function, and/or for the prevention and/or treatment of radiation-induced lung injury and lung complications, wherein the method comprises administering, to a patient or subject in need of such treatment, an effective amount of a composition comprising, consisting essentially of, or consisting of one or more free amino acids selected from lysine, glycine, threonine, valine, tyrosine, aspartic acid, isoleucine, tryptophan, asparagine, and serine; one or more electrolytes; and optionally, therapeutically acceptable carriers, electrolytes, buffering agents, and flavoring agents.

In one specific embodiment, the subject invention provides a method for improving pulmonary function, and/or for the prevention and/or treatment of radiation-induced lung injury and lung complications, wherein the method comprises administering, to a patient or subject in need of such treatment, an effective amount of a composition comprising, consisting essentially of, or consisting of L-lysine, L-glycine, L-threonine, L-valine, L-tyrosine, L-aspartic acid, L-isoleucine, and L-serine; one or more electrolytes selected from $Na^+$, $Ca^{2+}$, $Mg^{2+}$, $HCO_3^-$, and $Cl^-$; and optionally, therapeutically acceptable carriers, buffering agents, and flavoring agents.

In one embodiment, the subject invention can be used to prevent and treat lung complications induced by radiation. In certain embodiments, the subject invention can be used to prevent and treat radiation-induced lung complications including, but not limited to, alveolitis, pneumonitis, and pulmonary fibrosis.

In one embodiment, the therapeutic composition is administered to a subject that received radiation, and the composition can be administered before, during, or after irradiation.

In one embodiment, the subject invention can be used to prevent and treat lung complications induced by lung injury or lung inflammation. In one embodiment, the composition can be administered to a patient or subject immediately before, during, and/or after injury to the lungs, and can be administered once or multiple times each day.

In certain embodiments, the subject invention can be used to prevent and treat pneumonitis, pulmonary fibrosis and/or other lung diseases or complications induced by radiation (such as ionizing radiation), cytotoxic chemotherapeutic agents, proton therapy; pollutants, toxins, trauma, cigarette smoking, autoimmune diseases such as rheumatoid arthritis, medications (e.g., amiodarone, bleomycin, busulfan, methotrexate, and nitrofurantoin), asbestos, and/or infection (e.g. viral, bacterial, fungal and parasitic infection).

In certain embodiments, the present invention can be used to treat lung diseases including, bronchial asthma, pneumonia, bronchiectasis, interstitial lung diseases, acute and/or chronic pneumonitis, chronic obstructive pulmonary disease (COPD), asthma, silicosis, and lung injury.

In certain embodiments, the subject invention can be used to prevent and/or treat pneumonitis and/or pulmonary fibrosis in subjects that receive radiation therapy for cancer or tumor.

In certain embodiments, the subject invention can be used to prevent and/or treat pneumonitis and/or pulmonary fibrosis in subjects that are accidentally exposed to radiation, such as for example, astronauts and pilots who are routinely exposed to space radiation, and subjects exposed to radiation due to nuclear accident, acts of war, or terrorism.

The term "pulmonary fibrosis" or "lung fibrosis", as used herein, refers to abnormal formation or accumulation of fibrous, connective, or scar tissues and/or matrix macromolecules (e.g., collagens, fibronectins, proteoglycans) on and/or within lungs.

The term "pneumonitis," as used herein, refers to its ordinary meaning, which is inflammation of lung tissue.

The term "treatment" or any grammatical variation thereof (e.g., treat, treating, and treatment etc.), as used herein, includes but is not limited to, alleviating a symptom of a disease or condition; and/or reducing, suppressing, inhibiting, lessening, or affecting the progression, severity, and/or scope of a disease or condition.

The term "prevention" or any grammatical variation thereof (e.g., prevent, preventing, and prevention etc.), as used herein, includes but is not limited to, delaying the onset of symptoms, preventing relapse to a disease, increasing latency between symptomatic episodes, or a combination thereof. Prevention, as used herein, does not require the complete absence of symptoms.

The term "effective amount," as used herein, refers to an amount that is capable of treating or ameliorating a disease or condition or otherwise capable of producing an intended therapeutic effect.

The term "subject" or "patient," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; domesticated and laboratory animals such as dogs, cats, horses, cattle, pigs, sheep, goats, chickens, mice, rats, guinea pigs, and hamsters.

In one embodiment, the subject or patient in need of treatment of the invention has received, or will receive, radiation (such as ionizing radiation) at a dose capable of causing lung injury. In certain embodiments, the subject or patient in need of treatment of the invention has received, or will receive, radiation at a dose of at least 1, 2, 3, 4, 5, 6, 7, 8, 9, 10, 15, 20, 25, 30, 35, 40, 45, 50, 55, 60, 65, 70, 80, 85, 90, 95, or 100 Gy. In certain embodiments, the subject or patient in need of treatment of the invention has received, or will receive, radiation at a dose at least 0.1, 0.3, 0.5, 0.7, 0.9, 1.0, 1.1, 1.2, 1.3, 1.4, 1.5, 1,6, 1.7, 1.8, 1.9, 2.0, 2.1, 2.2, 2.3, 2.4, 2.5, 2,7, 3.0, 3.2, 3.5, or 4.0 Gy per day.

In one embodiment, the subject or patient in need of treatment of the invention has received, or will receive, thoracic radiation.

In one embodiment, the subject or patient in need of treatment of the invention has lung injury, lung inflammation, or lung infection.

In one embodiment, the subject invention does not encompass the prevention or treatment of diseases, disorders, or complications in the gastrointestinal tract. In one embodiment, the subject invention does not encompass the prevention or treatment of diseases, disorders, or complications disclosed in PCT/US2011/053265, entitled Materials and Methods for Improving Gastrointestinal Function.

Formulations and Administration

The subject invention provides for therapeutic or pharmaceutical compositions comprising a therapeutically effective amount of the subject composition and, optionally, a pharmaceutically acceptable carrier. Such pharmaceutical carriers can be sterile liquids, such as water. The therapeutic composition can also comprise excipients, adjuvants, flavoring agents, etc. In an embodiment, the therapeutic composition and all ingredients contained therein are sterile.

In one embodiment, the therapeutic composition of the subject invention is formulated for oral administration. In another embodiment, the therapeutic composition of the subject invention is formulated for pulmonary administration.

The term "carrier" refers to a diluent, adjuvant, excipient, or vehicle with which the compound is administered. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient.

The invention also provides a pharmaceutical pack or kit comprising one or more containers filled with one or more of the ingredients, e.g., compound, carrier, or the pharmaceutical compositions of the invention.

In certain embodiments, the compositions are prepared in a form adapted for delivery into the lungs. For instance, the liquid pharmaceutical composition may be lyophilized prior to use in pulmonary delivery, where the lyophilized composition is milled to obtain the finely divided dry powder consisting of particles within a desired size range. For another instance, spray-drying may be used to obtain a dry powder form of the liquid pharmaceutical composition, and the process is carried out under conditions that result in a substantially amorphous finely divided dry powder consisting of particles within the desired size range. For methods of preparing dry powder forms of pharmaceutical compositions, see, for example, WO 96/32149; WO 97/41833; WO 98/29096; and U.S. Pat. Nos. 5,976,574; 5,985,248; 6,001,336; and 6,875,749 herein incorporated by reference. In addition, the dry powder form of the pharmaceutical composition may be prepared and dispensed as an aqueous or nonaqueous solution or suspension, in a metered-dose inhaler.

A surfactant may be added to the pharmaceutical composition to reduce adhesion of the dry powder to the walls of the delivery device from which the aerosol is dispensed. Suitable surfactants for this intended use include, but are not limited to, sorbitan trioleate, soya lecithin, and oleic acid. Devices suitable for pulmonary delivery of a dry powder form of a composition as a nonaqueous suspension are commercially available. Examples of such devices include the Ventolin metered-dose inhaler (Glaxo Inc., Research Triangle Park, N.C.) and the Intal Inhaler (Fisons, Corp., Bedford, Mass.). See also the aerosol delivery devices described in U.S. Pat. Nos. 5,522,378; 5,775,320; 5,934,272; and 5,960,792 herein incorporated by reference.

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; and Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., 1985, Science 228:190; During et al., 1989, Ann. Neurol. 25:351; Howard et al., 1989, J. Neurosurg. 71:105).

In one embodiment, the pharmaceutical pack or kit further comprises instructions for administration, for example, with respect to effective therapeutic doses, and/or the timing of administration with reference to, for example, the elapse time from the exposure to radiation, chemotherapy, or proton therapy. For instance, with regard to subjects that receive, or are about to receive, radiation, the therapeutic dose of the composition is determined based on radiation sources, the body part being irradiated, and/or the time that has elapsed after irradiation. With regard to subjects that receive, or are about to receive chemotherapy, the therapeutic dose of the composition is determined based on the type of chemotherapeutic agents, the dosage of chemotherapeutic agent, and/or the time that has elapsed after chemotherapy. With regard to subjects that receive, or are about to receive, proton therapy, the therapeutic dose of the composition is determined based on the dosages of proton therapy received by the subject, and/or the time that has elapsed after proton therapy.

The compositions of the subject invention can be administered to the subject being treated by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a subject.

EXAMPLE

Following is an example that illustrates procedures and embodiments for practicing the invention. The example should not be construed as limiting.

Example 1

Therapeutic Compositions for Improving Pulmonary Function

This Example provides formulations for improving lung function, as well as for prevention and/or treatment of lung complications induced by radiation.

| Formulation 1 (Serving Size 1 bottle (237 ml)) | | |
|---|---|---|
| | Amount per serving | % Daily Value |
| Calories | 10 | |
| Chloride | 550 mg | 16% |
| Sodium | 370 mg | 15% |
| Salt Blend 929 mg | | |
| Sodium Chloride, Calcium Chloride, Magnesium Chloride | | |
| L-Valine | 276 mg | |
| L-Aspartic Acid | 252 mg | |
| L-Serine | 248 mg | |
| L-Isoleucine | 248 mg | |
| L-Threonine | 225 mg | |
| L-Lysine HCL | 172 mg | |
| L-Glycine | 141 mg | |
| L-Tyrosine | 51 mg | |
| Other Ingredients: Water, Natural Flavor, Sodium Bicarbonate | | |

| Formulation 2 (Serving Size 1 bottle (237 ml)) |
|---|
| Amount per serving |
| Calories 10 |

| | % Daily Value |
|---|---|
| Total Fat 0 g | 0% |
| Sodium 440 mg | 18% |
| Total Carbohydrate 0 g | 0% |
| Protein 2 g | |
| Ingredients: Water, Amino Acids (L-Tryptophan, L-Valine, L-Aspartic Acid, L-Serine, L-Isoleucine, L-Threonine, L-Lysine Hydrochloride, L-Glycine, L-Tyrosine), Salt, Natural Flavor, Sodium Bicarbonate, Calcium Chloride, Magnesium Chloride | |

-continued

Formulation 2
(Serving Size 1 bottle (237 ml))

| Amino Acid | Amount mg/1 bottle serving (237 ml) |
| --- | --- |
| L-Lysine HCl | 175 |
| L-Aspartic Acid | 255 |
| L-Glycine | 144 |
| L-Isoleucine | 251 |
| L-Threonine | 228 |
| L-Tyrosine | 52 |
| L-Valine | 281 |
| L-Tryptophan | 392 |
| L-Serine | 252 |

Mice received radiation at a dose of 8 Gy. Twenty-four hours after irradiation, mice are treated with the therapeutic composition of the subject invention for a period of 14 days. Six months after irradiation, pulmonary function test, electrophysiology, radiological and histopathological examinations are performed.

Figure 1B:
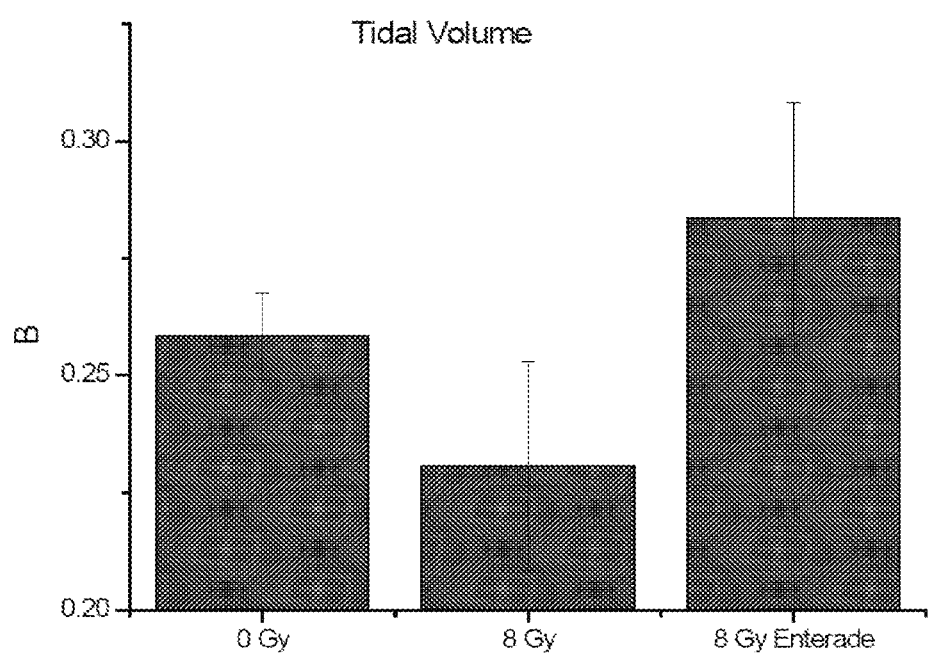
Figure 1C:
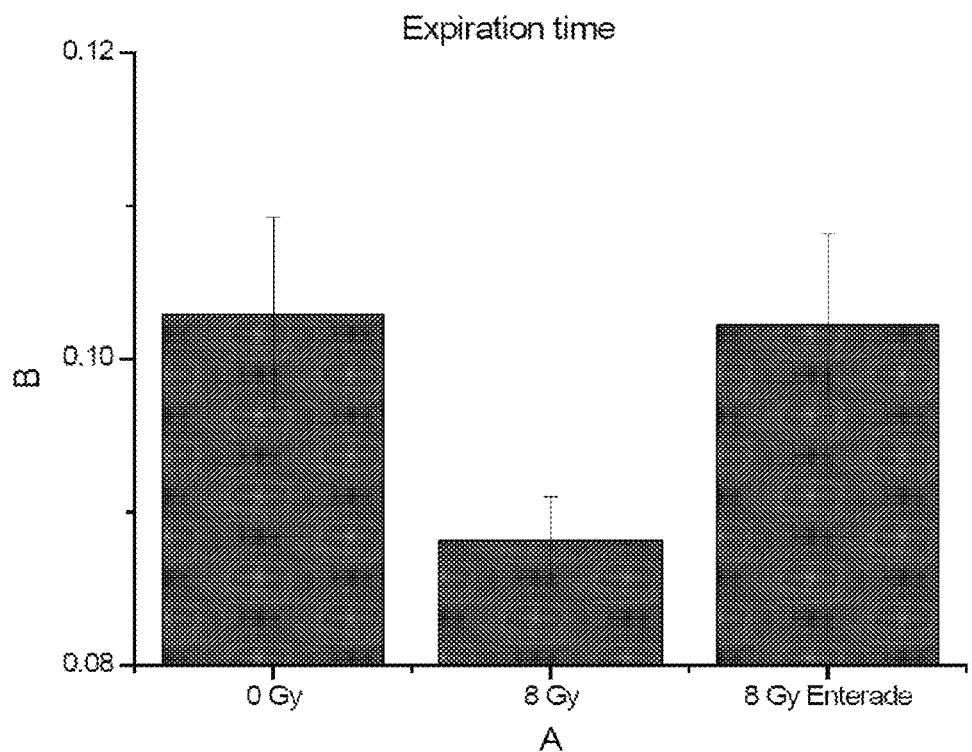
Figure 1D:
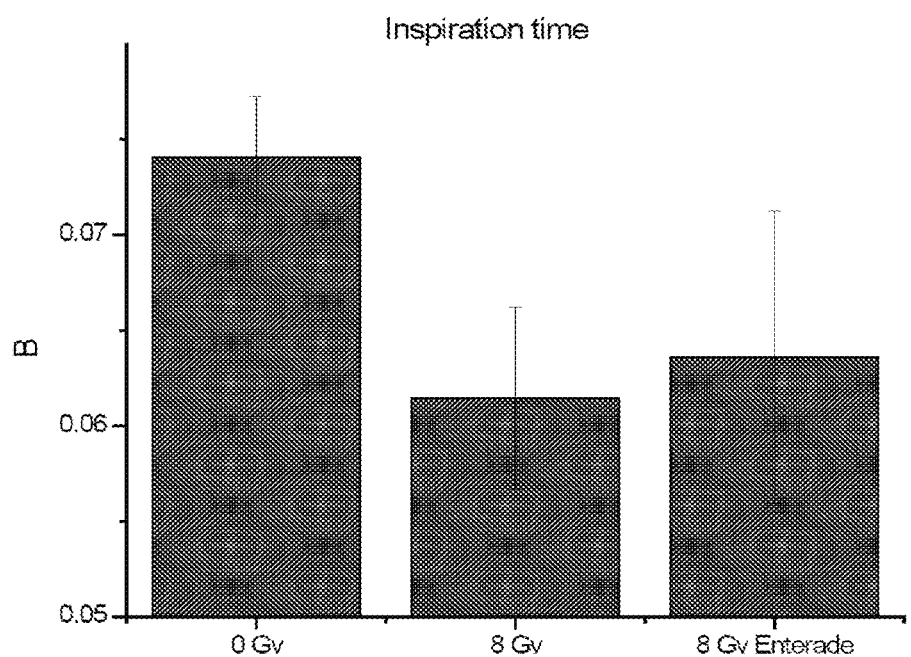
Figure 1E:
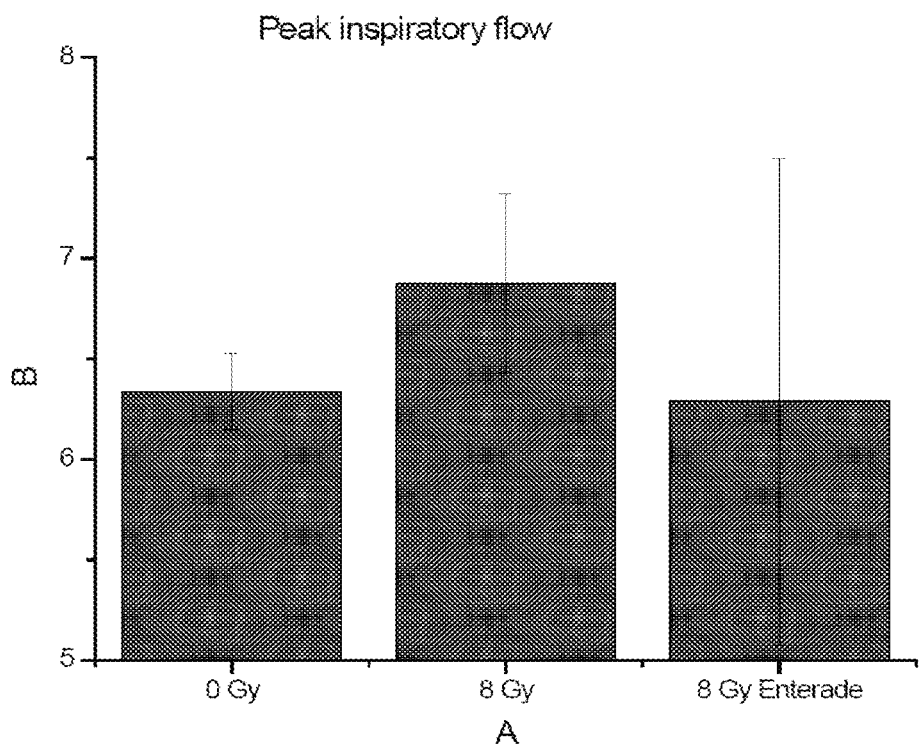
Figure 1F:
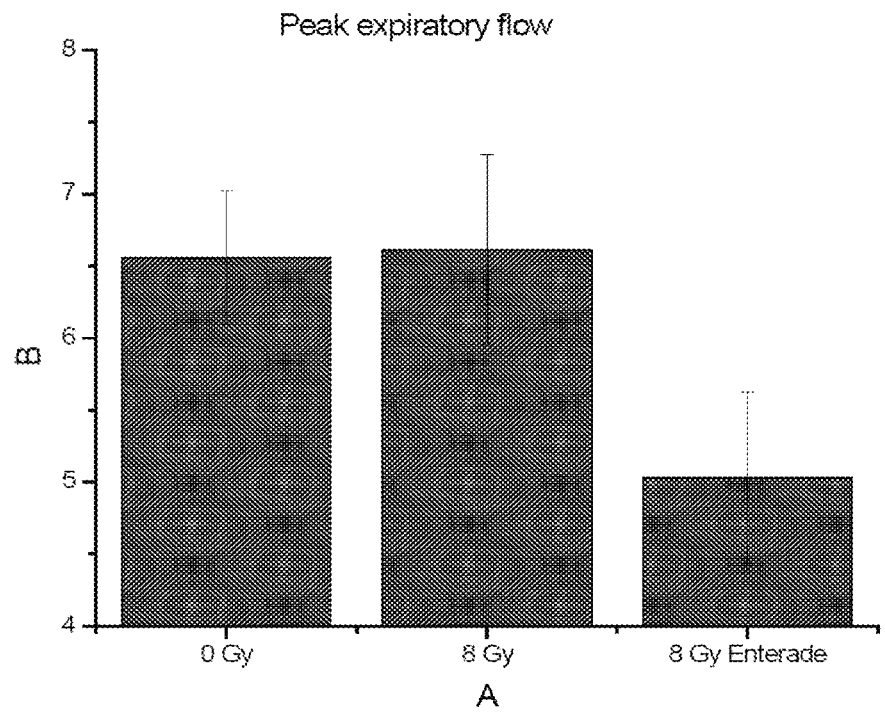
Figure 1G:
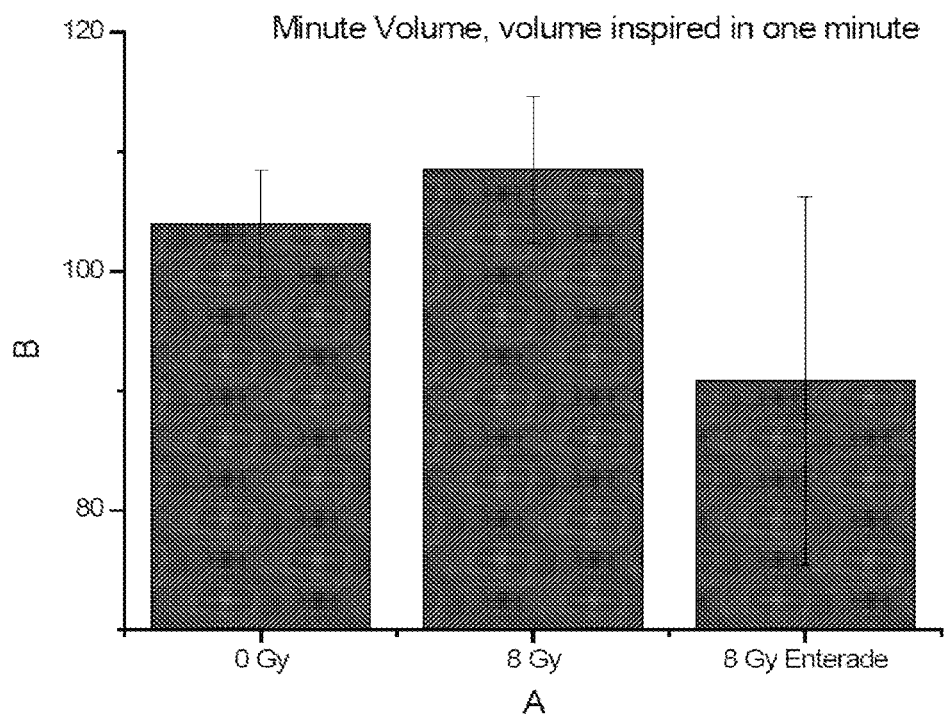
Figure 1H:
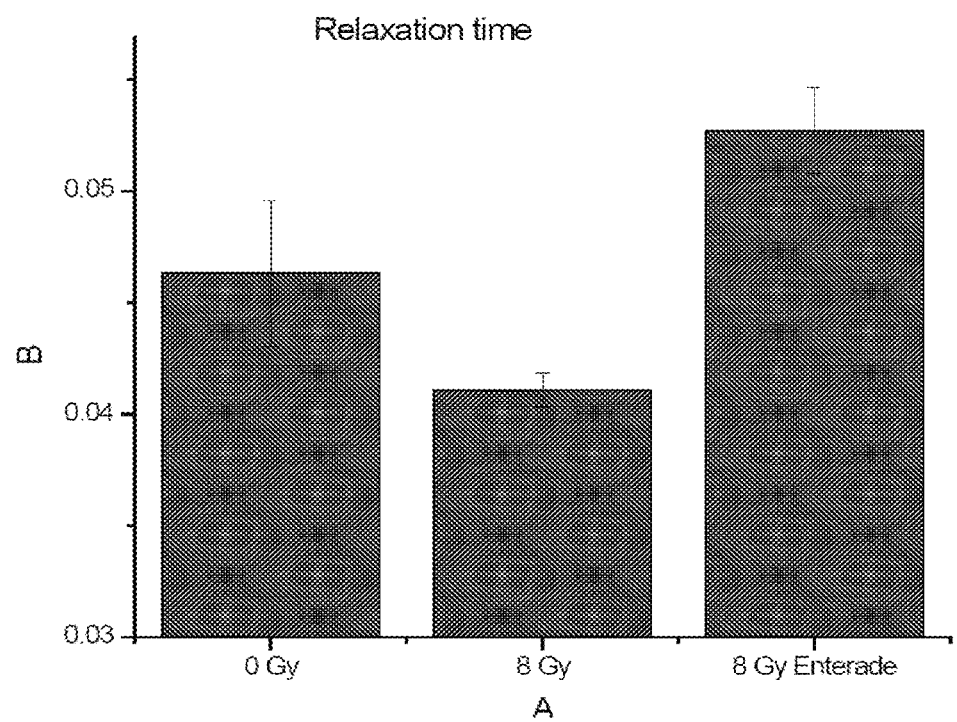

As shown in FIG. 1A-G, mice treated with the composition of the subject invention exhibit improved pulmonary function, electrophysiology, radiological and histopathological features.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

We claim:

1. A method for treating at least one lung complication induced by radiation in a human subject in need thereof, wherein the method comprises:
   administering, to the human subject in need thereof, an effective amount of a therapeutic formulation comprising free amino acids, the free amino acids consisting essentially of free amino acids of lysine, glycine, threonine, valine, tyrosine, aspartic acid, isoleucine, and serine; and
   optionally, tryptophan;
   wherein the human subject in need thereof receives radiation at a dose capable of causing lung injury,
   wherein the therapeutic formulation is administered via inhalation, and
   wherein the effective amount is sufficient to improve pulmonary function impaired by the at least one lung complication induced by radiation in the human subject in need thereof.

2. The method of claim 1, wherein the human subject in need thereof receives radiation in a chest area at a dose capable of causing lung injury.

3. The method of claim 1, wherein the therapeutic formulation further comprises therapeutically acceptable carriers, electrolytes, buffering agents, vitamins, or flavoring agents, or any combination thereof.

4. The method of claim 1, wherein the therapeutic formulation consists essentially of L-lysine, L-glycine, L-threonine, L-valine, L-tyrosine, L-aspartic acid, L-isoleucine, and L-serine; and optionally, therapeutically acceptable carriers, electrolytes, buffering agents, vitamins, or flavoring agents, or any combination thereof.

5. The method of claim 1, wherein the therapeutic formulation comprises one or more electrolytes selected from Na+, Ca2+, Mg2+, HCO3−, and Cl−.

6. The method of claim 1, wherein the therapeutic formulation has a total osmolarity from 165 mOsm to 300 mOsm.

7. The method of claim 1, wherein the therapeutic formulation is administered before, during, or after irradiation, or any combination thereof.

8. The method of claim 1, wherein the lung complication induced by radiation is radiation-induced alveolitis, radiation-induced pneumonitis, or radiation-induced pulmonary fibrosis, or any combination thereof.

9. The method of claim 1, wherein the human subject in need thereof is a pilot or astronaut.

10. The method of claim 1, wherein the therapeutic formulation consists essentially of L-lysine, L-glycine, L-threonine, L-valine, L-tyrosine, L-aspartic acid, L-isoleucine, L-serine, and L-tryptophan; and optionally, therapeutically acceptable carriers, electrolytes, buffering agents, vitamins, or flavoring agents, or any combination thereof.

11. The method of claim 10, wherein the therapeutic formulation comprises one or more electrolytes selected from Na+, Ca2+, Mg2+, HCO3−, and Cl−.

12. The method of claim 10, wherein the therapeutic formulation has a total osmolarity from 165 mOsm to 300 mOsm.

13. The method of claim 10, wherein the therapeutic formulation is administered before, during, or after irradiation, or any combination thereof.

14. The method of claim 10, wherein the lung complication induced by radiation is radiation-induced alveolitis, radiation-induced pneumonitis, or radiation-induced pulmonary fibrosis, or any combination thereof.

15. The method of claim 10, wherein the human subject in need thereof is a pilot or astronaut.

* * * * *